United States Patent [19]

Pepper et al.

[11] Patent Number: 5,118,003
[45] Date of Patent: Jun. 2, 1992

[54] VACUUM DRAINAGE COLLECTING DEVICE

[75] Inventors: Kenneth V. Pepper, Plymouth; Joseph M. Hand, Sheboygan Falls, both of Wis.

[73] Assignee: Bemis Manufacturing Company, Sheboygan Falls, Wis.

[21] Appl. No.: 613,264

[22] Filed: Nov. 9, 1990

Related U.S. Application Data

[63] Continuation-in-part of Ser. No. 372,702, Jun. 26, 1989, abandoned.

[51] Int. Cl.⁵ .............................................. B65D 25/16
[52] U.S. Cl. ..................................... 220/404; 220/307; 215/341; 222/105
[58] Field of Search ................... 222/95, 105, 386.5; 383/33; 215/341, 317; 220/403, 404, 470, 306, 307, 308

[56] References Cited

U.S. PATENT DOCUMENTS

| | | | |
|---|---|---|---|
| 2,105,160 | 1/1938 | Piquerez | 222/386.5 |
| 2,196,785 | 4/1940 | Takiguchi | 215/47 |
| 2,338,604 | 1/1944 | Silveyra | 229/14 |
| 2,757,669 | 8/1956 | Gewecke et al. | 128/214 |
| 2,912,136 | 11/1959 | Redmond et al. | 220/63 |
| 3,458,079 | 7/1969 | Gasbarra | 220/308 |
| 3,578,200 | 5/1971 | Hetzer | 220/42 B |
| 3,620,399 | 11/1971 | Rapeaud | 220/404 |
| 3,648,875 | 3/1972 | Lundgren | 220/1 T |
| 3,664,535 | 5/1972 | Mette | 215/11 R |
| 3,680,560 | 8/1972 | Pannier, Jr. et al. | 128/276 |
| 3,680,568 | 8/1972 | James et al. | 134/63 |
| 3,773,211 | 11/1973 | Bridgman | 220/63 R |
| 3,834,570 | 9/1974 | Barr | 220/403 |
| 3,913,780 | 10/1975 | Holbrook et al. | 220/306 |
| 4,245,753 | 1/1981 | Ellis | 220/307 |
| 4,245,754 | 1/1981 | Ellis | 220/306 |
| 4,293,353 | 10/1981 | Pelton et al. | 222/95 |
| 4,298,134 | 11/1981 | Lewis, Jr. | 220/306 |
| 4,321,922 | 3/1982 | Deaton | 128/276 |
| 4,379,455 | 4/1983 | Deaton | 604/320 |
| 4,430,084 | 2/1984 | Deaton | 604/317 |
| 4,431,110 | 2/1984 | Roth | 215/213 |
| 4,598,838 | 7/1986 | Zakrajsek | 220/404 |
| 4,620,641 | 11/1986 | Beer | 220/307 |
| 4,687,115 | 8/1987 | Bongiovanni | 215/355 |
| 4,883,194 | 11/1989 | Fernandes | 220/307 |

FOREIGN PATENT DOCUMENTS

| | | | |
|---|---|---|---|
| 407138 | 10/1970 | Australia | 215/341 |
| 3521866 | 1/1987 | Fed. Rep. of Germany. | |
| 1158278 | 7/1969 | United Kingdom. | |

Primary Examiner—Stephen Marcus
Assistant Examiner—S. Castellano
Attorney, Agent, or Firm—Michael, Best & Friedrich

[57] ABSTRACT

A disposable cover and bag assembly comprising an outer cover member adapted to be connected to the open end of an outer canister and having a top including therein an opening, an inner cover member in the opening in the top of the outer cover member, and a bag having a mouth gripped between the inner and outer cover members.

22 Claims, 4 Drawing Sheets

VACUUM DRAINAGE COLLECTING DEVICE

RELATED APPLICATION

This is a continuation-in-part of U.S. Ser. No. 372,702, filed Jun. 26, 1989, now abandoned.

BACKGROUND OF THE INVENTION

1. Field of the Invention

The invention relates generally to collection devices and, more particularly, to vacuum operated and at least partially disposable collection devices.

Still more particularly, the invention relates to collection devices including a flexible bag or liner which is supported by a canister cover and located within a rigid canister connected to the canister cover.

2. Reference to the Prior Art

In the past, liners or bags have been secured to a canister cover by heat sealing and/or by the use of a heat sealant. Bags or liners made from a plasticized flexible polyvinylchloride can be welded by using electrodes and a radio frequency electrical supply. When a flexible bag or liner is composed of polyethylene it can be welded or fused to a stiffer polyethylene canister cover by using a heated electrode.

Whatever materials have been used in the past to manufacture the bag or liner and the canister cover, all such products have relied on fusing the bag or liner to the canister cover. Furthermore, and in order to facilitate such fusing, both the bag or liner and the canister cover have been made from compatible materials, for example, flexible polyvinylchloride to rigid polyvinylchloride, or low-density polyethylene to high-density polyethylene. In all cases, uniform and controlled pressure has to be applied at the point of attachment of the bag or liner to the canister cover. In addition, the energy applied, whether resistance or radio frequency current, has to be accurately controlled, as does the duration of its application. Fluctuations in these conditions can lead to missed areas or weak areas of fusion when the heat, pressure, or duration is insufficient, or the electrode may push through the wall of the thin bag or liner when the heat, pressure, or duration is excessive. Suffice to say that the process of fusing the two parts together is such as to lead to a percentage of rejects and to frequent testing to ensure that conditions are optimum.

Any product requiring two parts to be fused together must employ parts of compatible material. Such compatibility requirements would have to take precedence over optimum performance for each part. While flexible plasticized polyvinylchloride not only affords crystal clarity but great flexibility, properties very desirable in a bag or liner, such material cannot be fused to a high-density polyethylene canister cover whose properties most suit the performance of the canister cover.

Attention is directed to U.S. Pat. No. 3,680,560 dated Aug. 1, 1972.

SUMMARY OF THE INVENTION

The invention provides a disposable cover and bag assembly comprising a lower cover member including a top having therein an opening, an upper cover member closing the opening in the top of the outer cover member, and a bag having a mouth gripped between the cover members, one of the cover members being adapted to be connected to the open end of an outer canister, and the cover members including inter-engaging means affording assembly of the cover members and preventing disassembly of the cover members, the inter-engaging means comprising a serrated formation on each of the cover members, the serrated formation on the lower cover member including a plurality of projections having downwardly sloped upper surfaces and generally horizontal lower surfaces, the serrated formation on the upper cover member including a plurality of projections having upwardly sloped lower surfaces and generally horizontal upper surfaces, and the bag being clamped between the formations.

The invention also provides a disposable cover and bag assembly comprising a lower cover member including a top having therein an opening, an upper cover member closing the opening in the top of the outer cover member, and a bag having a mouth gripped between the cover members, one of the cover members being adapted to be connected to the open end of an outer canister, and the cover members including inter-engaging means affording assembly of the cover members and preventing disassembly of the cover members, the inter-engaging means comprising a plurality of vertically spaced and horizontally offset projections on the lower cover member, and a plurality of vertically spaced and horizontally offset projections on the upper cover member, and the bag being clamped between the projections on the upper and lower cover members.

The invention also provides a disposable cover and bag assembly comprising a lower cover member including a top having therein an opening, an upper cover member closing the opening in the top of the outer cover member, and a bag having a mouth gripped between the cover members, one of the cover members being adapted to be connected to the open end of an outer canister, and the cover members including inter-engaging means affording assembly of the cover members and preventing disassembly of the cover members, the inter-engaging means comprising a non-threaded serrated formation on each of the cover members, each of the serrated formations including a plurality of parallel, endless projections defining grooves there between, the projections of each of the formations being received in the grooves of the other of the formations, and the bag being clamped between the formation.

The invention also provides a disposable cover and bag assembly comprising an outer cover member adapted to be connected to the open end of an outer canister and having a top including therein an opening, an inner cover member in the opening in the top of the outer cover member, and a bag having a mouth gripped between the inner and outer cover members, the inner and outer cover members including inter-engaging means affording assembly of the inner and outer cover members and preventing disassembly of the inner and outer cover members, the inter-engaging means comprising a non-threaded serrated formation on each of the inner and outer cover members, each of the serrated formations including a plurality of parallel, endless projections defining grooves there between, the projections of each of the formations being received in the grooves of the other of the formations, and the bag being clamped between the formations.

The invention also provides a collection apparatus with a disposable portion comprising an outer canister having an open end, an outer cover member detachably connected to the open end and having a top including therein an opening, an inner cover member in the opening in the top of the outer cover member, and a bag extending in the outer canister and having a mouth gripped between the inner and outer cover members, the inner and outer cover members including inter-engaging means affording assembly of the inner and outer cover members and preventing disassembly of the inner and outer cover members, the inner-engaging means comprising a non-threaded serrated formation on each of the inner and outer cover members, each of the serrated formations including a plurality of parallel, endless projections defining grooves there between, the projections of each of the formations being received in the grooves of the other of the formations, and the bag being clamped between the formations.

The invention also provides a disposable cover and bag assembly comprising an outer cover member adapted to be connected to the open end of an outer canister and having a top including therein an opening, an inner cover member in the opening in the top of the outer cover member, a bag having a mouth gripped between the inner and outer cover members, and means on the inner and outer cover members for clamping the bag there between, the means including on one of the cover members a serrated formation for cammingly engaging the other of the cover members and for clamping the bag between the serrated formation and the other of the cover members.

The invention also provides a collection apparatus with a disposable portion comprising an outer canister having an open end, an outer cover member detachably connected to the open end and having a top including therein an opening, an inner cover member in the opening in the top of the outer cover member, a bag extending in the outer canister and having a mouth gripped between the inner and outer cover members, and means on the inner and outer cover members for clamping the bag there between, the means including on one of the cover members a serrated formation for cammingly engaging the other of the cover members and for clamping the bag between the serrated formation and the other of the cover members.

One of the features of the invention is to use otherwise incompatible materials for the bag or liner and for the canister cover, each chosen for its specific duty.

Other features and advantages of the invention will become apparent to those skilled in the art upon review of the following detailed description, claims, and drawings.

THE DRAWINGS

Figure 1:
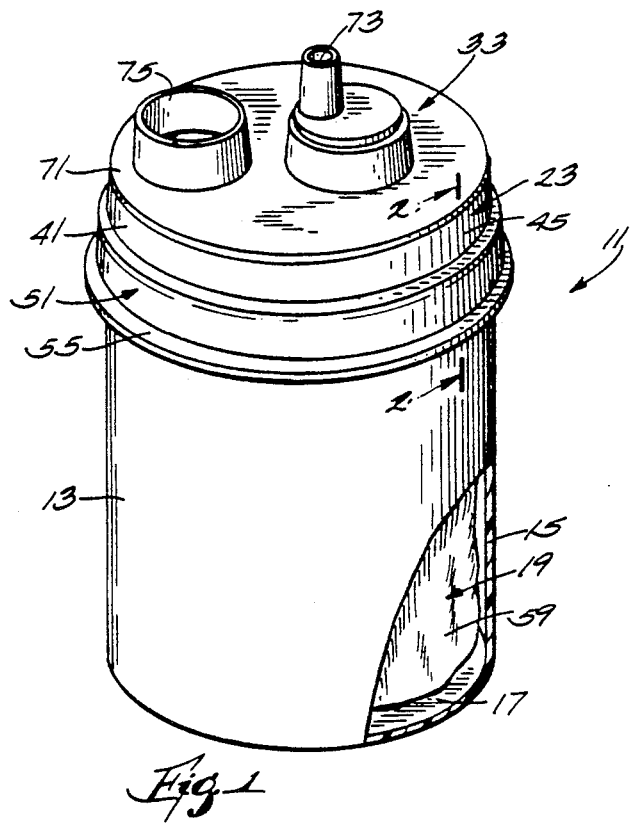
FIG. 1 is a partially broken away and sectioned perspective view of a collection device embodying various of the features of the invention.
Figure 2:
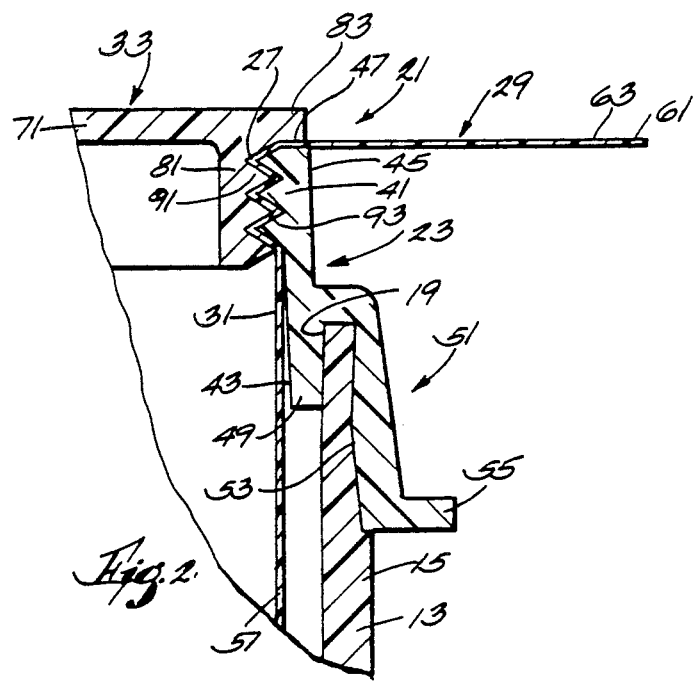
FIG. 2 is an enlarged, fragmentary, sectional view taken along line 2—2 of FIG. 1.
Figure 3:
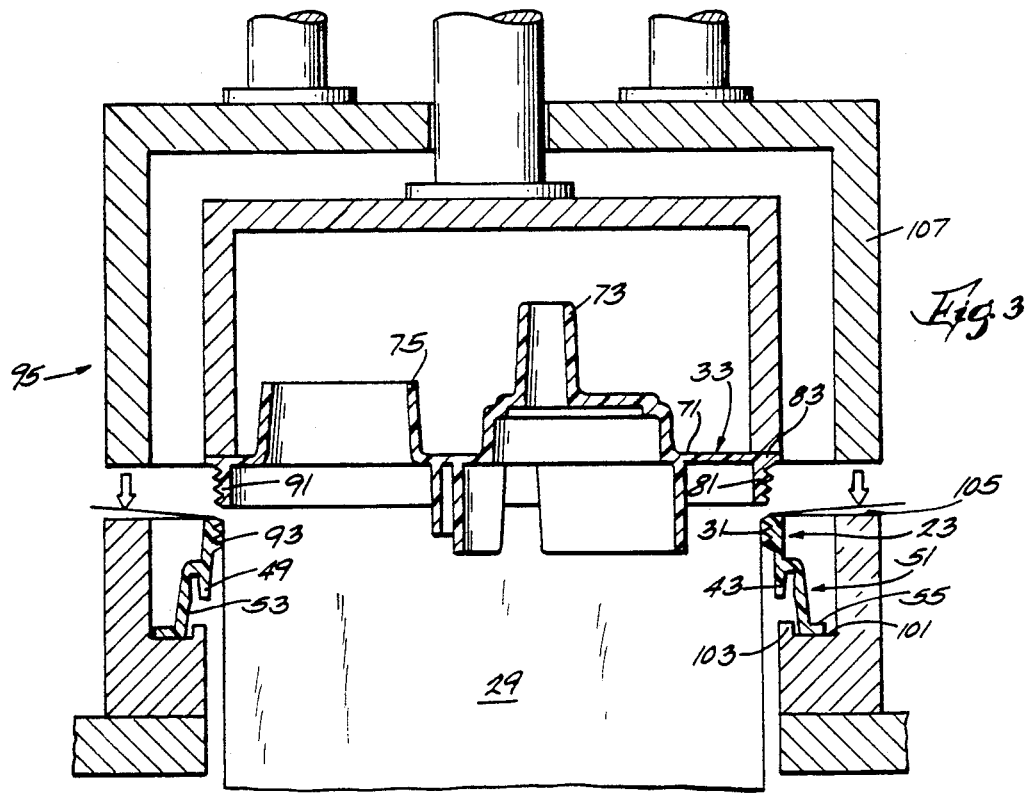
FIG. 3 is a partially schematic view of a device for assembling a cover and bag assembly embodied in the collection device shown in FIG. 1.
Figure 4:
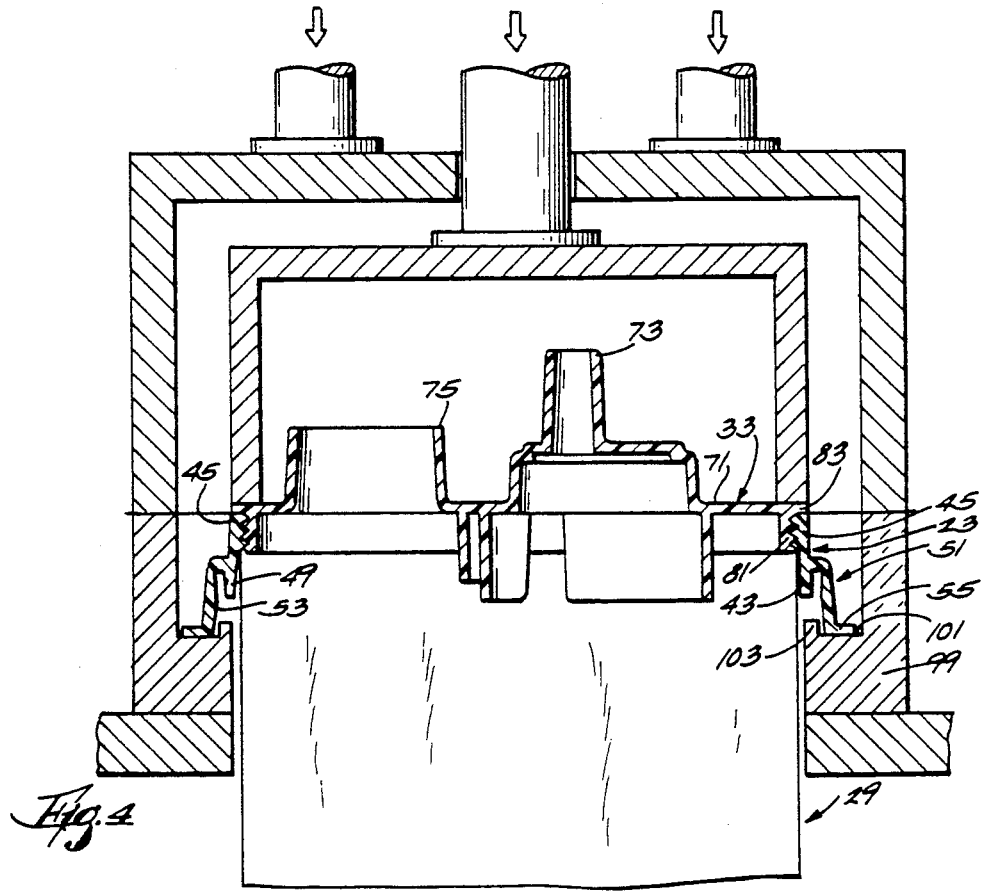
FIG. 4 is a view similar to FIG. 3, but illustrating certain components in somewhat different positions.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

GENERAL DESCRIPTION

Illustrated in the drawings is a vacuum drainage collection apparatus 11 including a rigid canister 13 having a continuous side wall 15, a closed bottom 17, and an open upper end or top 19.

Closing the open top 19 of the canister 13 is a disposable cover and bag assembly 21 including an outer or lower cover member or ring 23 having a top including therein an opening 27, a bag or liner 29 having an open mouth 31 extending through the opening 27 in the top of the outer cover member or ring 23, and an inner or upper cover member 33 extending into the mouth 31 of the bag 29 and gripping the outer cover member or ring 23 to clamp the mouth 31 of the bag between the outer and inner cover members 23 and 33.

More particularly, the canister 13 can be fabricated of any desired rigid material and can be either of metal or plastic.

The outer cover member or ring 23 can be fabricated of various materials, such as a propylene/ethylene co-polymer, or polypropylene, or a polyvinyl chloride-/ethyl vinyl acetate blend. In addition, semirigid thermoplastic elastomers can also be employed. The outer cover member or ring 23 includes a generally cylindrical main body section 41 having an inner surface 43 defining the opening 27, an outer surface 45, a top or upper surface 47 joining the inner and outer surfaces 43 and 45, and a lower end 49. The outer cover member or ring 23 also includes an outer supporting section 51 which extends from about the mid-portion of the outer surface 45 of the cylindrical section 41 and then downwardly therefrom, forming a cylindrical cavity or groove or space 53 for frictional receipt therein of the open upper end or top 19 of the rigid canister 13. Such receipt can afford a seal between the outer cover member or ring 23 and the canister 13, while, at the same time, affording disassembly of the canister 13 from the cover and bag assembly 21.

The supporting section 51 also includes, at the axially outer or lower end thereof, a radially outwardly extending flange or foot 55 for purposes to be disclosed hereinafter.

The bag or liner 29 can be formed of any desired flexible sheet plastic and comprises a main body 57 which extends into and, in general, occupies the volume within the rigid canister 13 and which incorporates a closed lower end 59. At its upper end, the main body 57 includes the open mouth 31 which has a size closely approximating the size of the opening 27 in the outer cover member or ring 23. In addition the bar or liner 29 includes a flange 61 extending radially outwardly across the top surface 47 of the outer cover member or ring 23 and includes a part 63 extending beyond the perimeter of the outer cover member or ring 23. As will hereinafter be explained, the part 63 of the flange extending beyond the outer cover member 23 is subsequently trimmer from the resulting cover and bag assembly 21.

The bag or liner 29 can be fabricated of various materials and is preferably fabricated from a flexible plasticized polyvinylchloride calendared sheet by cutting, forming and radio frequency welding or, preferably, is blow molded in one piece to provide a closed balloon prior to cutting off at one end, i.e., the top, leaving the bag or liner 29 with the extending flange or portion 61. Typically, and for example, the bag or liner 29 could have a wall thickness of 0.007" and a Shore A scale hardness of 85. Other materials which can be used for the bag or liner 29 include clear polyurethane, translucent, low, medium or high density polyethylene, and translucent polyethylene/ethylvinyl acetate copolymers.

As illustrated, the flange 61 is shown in a flat plane, perpendicular to the mouth 31 of the bag or liner 29. However, since as will be explained, the purpose of the flange 61 is to facilitate holding and clamping the bag or liner 29 during assembly of the bag 29 with the inner and outer cover members 23 and 33, and since, after assembly, the part of the flange extending beyond the outer cover member or ring 23 is automatically trimmed off, the specific form of the flange can be any other suitable shape, such as at an angle to the side wall of the bag or liner 29.

The inner cover member 33 can be fabricated of various materials and is preferably fabricated of relatively rigid plastic such as unplasticized polyvinylchloride. Other materials which can be employed include polypropylene and impact improved polystyrene. The inner cover member 31 comprises a main body or top wall 71 which includes a pouring spout, a vacuum passage 73 affording the creation of a vacuum in the bag or liner 29, a float, a schematically illustrated passage 75 through which fluids can be passed to the bag or liner 29 and a filter. These features in the top wall 71 are all known in the art and need not be further disclosed.

Also forming a part of the inner cover member 33 is a projecting cylindrical section 81 which projects downwardly from the top wall 71 and is inserted into the mouth 31 of the bag or liner 29 and into frictional engagement with the inner surface 43 of the cylindrical section 41 of the outer cover member or ring 23 so as to grip or clamp the mouth 31 of the bag or liner 29 between the inner and outer cover members 23 and 33. Preferably, the top wall 71 includes a rim 83 which extends radially and outwardly beyond the depending cylindrical section 81 and into covering relation to the top surface 47 of the outer cover member or ring 23.

As a consequence, the upper end of the bag or liner 29 is retained between the respective cylindrical sections 41 and 81 of the inner and outer cover members 23 and 33 and between the top surface 47 of the outer cover member or ring 23 and the outwardly extending rim 83 of the inner cover member 33.

Means are provided on the cylindrical sections 41 and 81 for inter-engagement there between to tightly grip or clamp the mouth 31 of the bag or liner 29 there between and to prevent disassembly of the inner and outer cover members 23 and 33.

While other constructions can be employed, in the disclosed construction, such means comprises, on each of the inner and outer cover members 33 and 23, respective serrated formations 91 and 93 in the form of a series of serrations provided by a series of annular parallel projections and grooves which form annular teeth, which serrated formations can, in the presence of suitable axial force, be inter-fitted to prevent subsequent disassembly of the inner and outer cover members 23 and 33 and, at the same time, will effect tight clamping of the bag or liner 29 between the inner and outer members 23 and 33 without causing ripping or tearing of the mouth 31 of the bag or liner 29.

The serrations 91 and 93 are symmetrical in form, preferably having a 45° angle; and each serration or tooth is parallel to the other and is not helical as in a screw thread While the disclosed construction includes the illustrated pointed serrated formations 91 and 93, the serrations need not come to a point, but could be truncated. In addition, other constructions could be employed.

In assembly of the cover and bag assembly 21, the annular foot 55 of the outer cover member or ring 23 is placed on an anvil 99 having a supporting surface 101 of a mandrel or manual press 95 or other suitable machine, which anvil 99 includes an annular inner lip 103 extending into the annular space or cavity 53 formed at the lower end of the supporting section 51. The anvil 99 also extends upwardly in generally surrounding relation to the radially outer end of the annular foot 55 and terminates in an upper annular surface 105 which is generally co-planar with the top surface 47 of the outer cover member or ring 23.

A disposable bag or liner 29 is then dropped or inserted into and through the opening 27 in the top of the cylindrical section 41 of the outer cover member or ring 23 so that the mouth 31 of the bag or liner 29 contacts the inner surface 43 adjacent the top surface 47 and so that the flange 61 extends outwardly into over-lapping relation to the upper annular surface 105 of the press.

The flange 61 is then clamped or gripped to the upper annular surface 105 by an annular anchor ring 107 which is moved into engagement with the flange part 63 to hold the flange part 63 tightly between the anchor ring 107 and the upper annular surface 105.

The inner cover member 33 is then located in the mouth 31 of the bag or lever 29 and pressed rapidly inwardly into the opening 27 until the rim 83 engages the top surface 47 of the outer cover member or ring 23. Such movement causes the outer cover member or ring 23 to expand within the elastic limit as the serrations engage. As a consequence the mouth 31 of the bag or liner 29 is now firmly gripped or clamped between the engaged serrations of the inner and outer cover members 23 and 33, and is thus deformed to duplicate the profile of the serrations.

Notwithstanding that the inner cover member 23 is placed under compression during assembly, the inner cover member, and in addition, the serrated formation, has inherent resistance to compressive loads. Furthermore, the cylindrical section 81 is reinforced by the top wall 71 of the inner cover member 33. As a consequence, the inner cover member 33 is minimally deformed. On the other hand, the outer cover member or ring 23 is free to expand and subsequently return to its original diameter (except for the interposition of the bag or liner 29). After assembly, the outer cover member or ring 23 maintains constant compression on the bag or liner 29.

When the inner and outer cover members 23 and 33 are molded size on size to provide the serrations or teeth, the bar or liner 29 with a 0.007" wall can be readily accommodated between the two cover members 23 and 33 without undesirably stretching the bag or liner material when the inner and outer cover members 23 and 33 are molded from high-density polyethylene. Bags or liners of heavier gauge can be accommodated, except that proportional clearances between the serrations have to be incorporated into the inner and outer cover members 23 and 33.

Thereafter, the anchor ring 107 is withdrawn, releasing the grip on the flange part 63 and the cover and bag assembly 21 can then be removed from the press. Subsequently, the flange part 63 extending from the cover and bag assembly 21 is trimmed from the cover and bag assembly 21 to provide a neat appearance. Still more subsequently, the rigid canister 13 can be removably assembled into the annular groove or space 53 in the bottom of the outer cover member or ring 23 to provide support for the contents to be delivered into the bag or lever 29.

Figure 5:
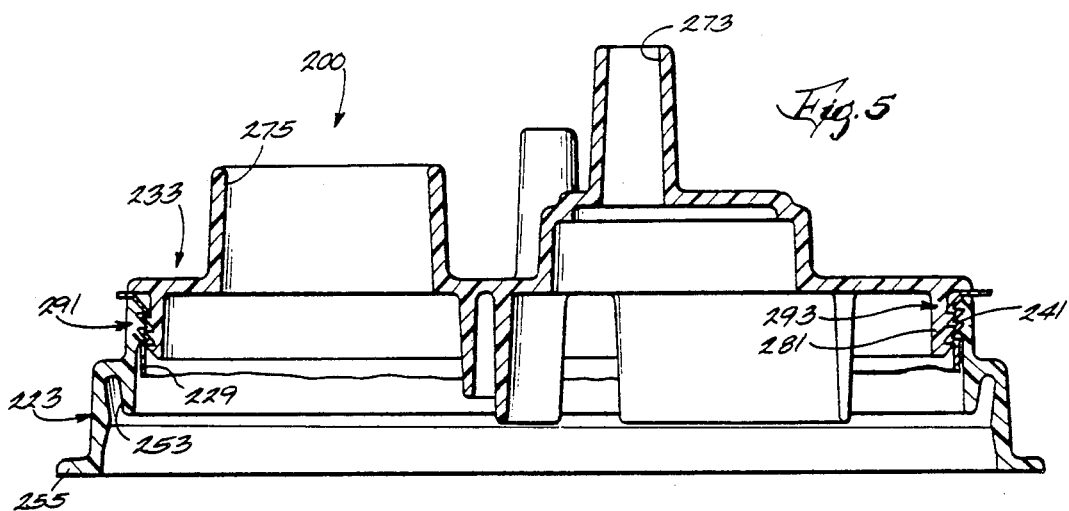
FIG. 5 is a fragmentary sectional view of a collection apparatus that is an alternative embodiment of the invention.
Figure 6:
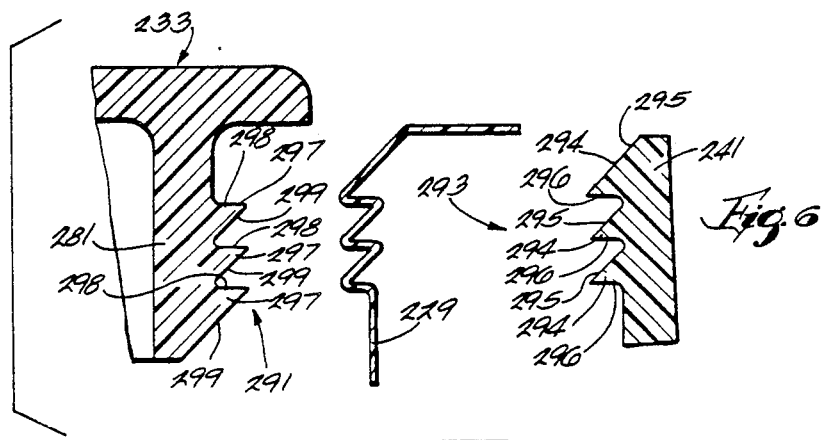
FIG. 6 is an enlarged, exploded, fragmentary sectional view of the apparatus shown in FIG. 5.

An apparatus 200 which is an alternative embodiment of the invention is illustrated in FIGS. 5 and 6. Except as described below, the apparatus 200 is substantially identical to the apparatus 11.

The apparatus 200 comprises (see FIG. 5) a lower cover member 223 including a groove 253 adapted to receive the upper end of the canister, and a foot 255. The lower cover member 223 also includes a cylindrical section 241 having thereon a non-threaded serrated formation 293. The serrated formation 293 includes (see FIG. 6) a plurality of annular, endless, parallel projections 294 defining grooves there between. Each of the projections 294 has a downwardly sloped upper surface 295 and a generally horizontal lower surface 296. The upper surface 295 is preferably sloped downwardly at an angle of approximately 45°.

The apparatus 200 also comprises (see FIG. 5) an upper cover member 233 including a vacuum passage 273 and a fluid passage 275. The upper cover member 233 also includes a cylindrical section 281 which is located inside the cylindrical section 241 of the lower cover member 223 when the apparatus 200 is assembled. The cylindrical section 281 has thereon (see FIG. 6) a non-threaded serrated formation 291 including a plurality of annular, parallel, endless projections 297 defining grooves there between. The projections 297 extend radially outwardly and each projection 297 has a generally horizontal upper surface 298 and an upwardly sloped lower surface 299. The lower surface 299 is preferably sloped upwardly at an angle of approximately 45°.

During assembly of the cover members 223 and 233 so as to clamp the bag 229 between the serrated formations 291 and 293, the upper surfaces 295 of the lower cover member 223 engage, through the bag 229, the lower surfaces 299 of the upper cover member 233. After assembly of the cover members 223 and 233, the lower surfaces 296 of the lower cover 223 member engage, through the bag 229, the upper surfaces 298 of the upper cover member 233 so as to prevent disassembly of the cover members 223 and 233. Furthermore, the projections 294 and 297 of each of the serrated formations are received in the grooves of the other of the formations.

The sloped surfaces 295 and 299 facilitate assembly of the cover members 223 and 233, while the horizontal surfaces 296 and 298 resist disassembly of the cover members.

Figure 7:
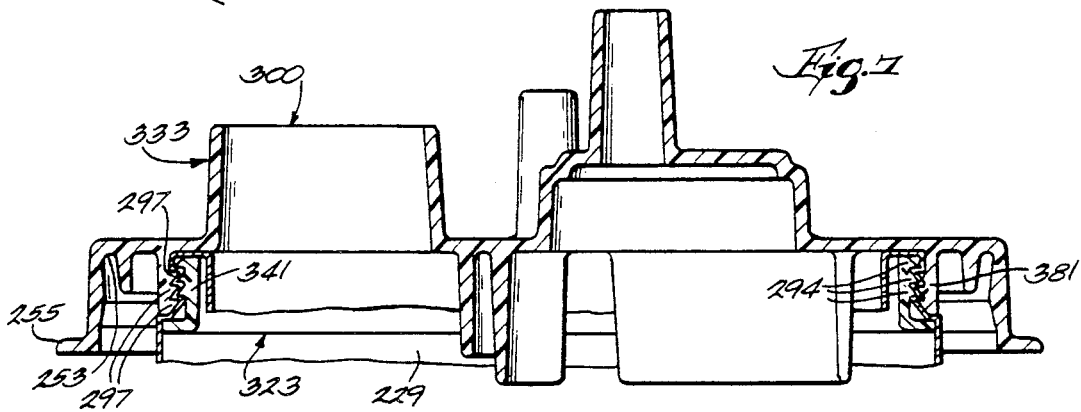
FIG. 7 is a view similar to FIG. 5 showing a second alternative embodiment of the invention.

An apparatus 300 which is a second alternative embodiment of the invention is illustrated in FIG. 7. Except as described below, the apparatus 300 is substantially identical to the apparatus 200, and corresponding elements have been given the same reference numerals.

The apparatus 300 comprises a lower cover member 323 having a cylindrical section 341, and an upper cover member 333 having therein a groove 253 and having thereon a foot 255. The upper cover member 333 has a cylindrical section 381 located outside the cylindrical section 341 of the lower cover member 323 when the apparatus 300 is assembled. The projections 294 on the lower cover member 323 therefore extend radially outwardly, and the projections 297 on the upper cover member 333 extend radially inwardly.

Figure 8:
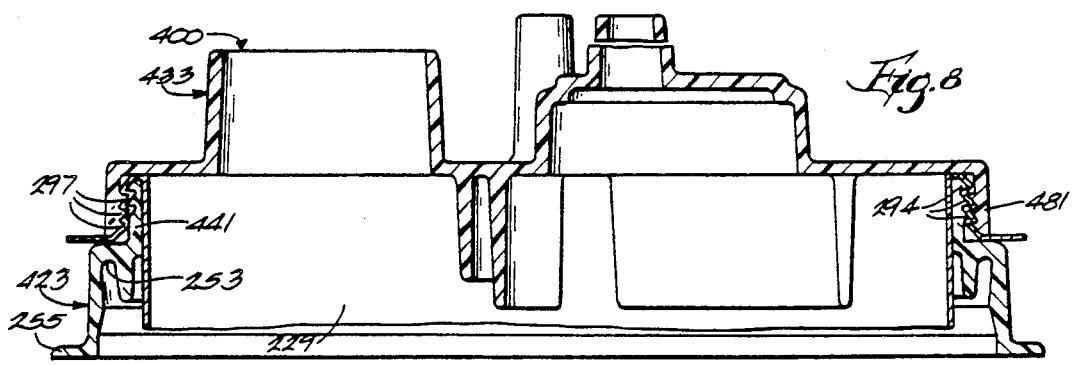
FIG. 8 is a view similar to FIG. 5 showing a third alternative embodiment of the invention.

An apparatus 400 which is a third alternative embodiment of the invention is illustrated in FIG. 8. Except as described below, the apparatus 400 is substantially identical to the apparatus 200, and corresponding elements have been given the same reference numerals.

Figure 9:
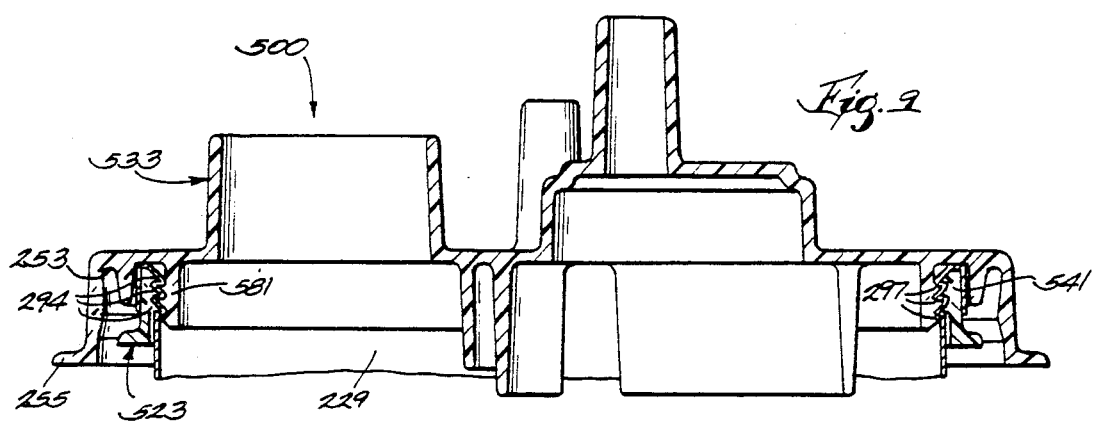
FIG. 9 is a view similar to FIG. 5 showing a fourth alternative embodiment of the invention.

The apparatus 400 comprises an upper cover member 433 having a cylindrical section 481, and a lower cover member 423 having therein a groove 253 and having thereon a foot 255. The lower cover member 423 also has a cylindrical section 441 located inside the cylindrical section 481 of the upper cover member 433 when the cover members are assembled. Accordingly, the projections 294 on the cylindrical section 441 extend radially outwardly, and the projections 297 on the cylindrical section 481 extend radially inwardly An apparatus 500 which is a fourth alternative embodiment of the invention is illustrated in FIG. 9. Except as described below, the apparatus 500 is substantially identical to the apparatus 200, and corresponding elements have been given the same reference numerals.

The apparatus 500 comprises an upper cover member 533 having a cylindrical section 581, having therein a groove 253, and having thereon a foot 255. The apparatus 500 also comprises a lower cover member 523 having a cylindrical section 541. The cylindrical section 541 of the lower cover member 523 is located outside the cylindrical section 581 of the upper cover member 533 when the cover members 233 are assembled. The projections 297 on the upper cover member 533 therefore extend radially outwardly, and the projections 294 on the lower cover member 523 extend radially inwardly.

The upper and lower cover members of each of the above-described apparatus each have thereon three projections 294 or 297. In order to assemble the cover members, the lower projection on the upper cover member must be "snapped" over all three projections on the lower cover member, the middle projection on the upper cover member must be snapped over two projections on the lower cover member, and the upper projection on the upper cover member must be snapped over one projection on the lower cover member. While the lower projection on the upper cover member is being snapped over the lower projection on the lower cover member, the middle and upper projections on the upper cover member are being simultaneously snapped over the middle and upper projections on the lower cover member. Thus, three projections on the upper cover member are being simultaneously snapped over respective projections on the lower cover member. This can make assembly difficult.

Figure 10:
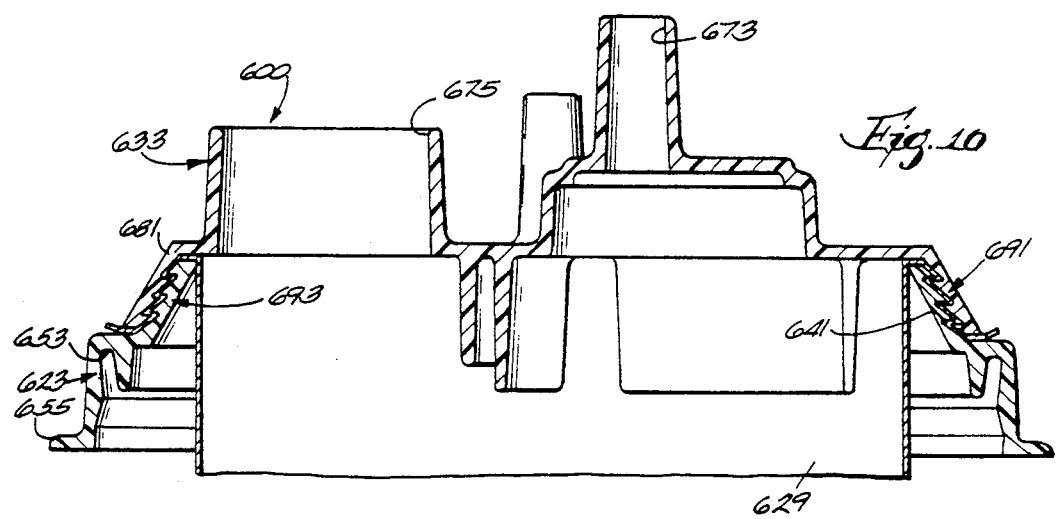
FIG. 10 is a view similar to FIG. 5 showing a fifth alternative embodiment of the invention.
Figure 11:
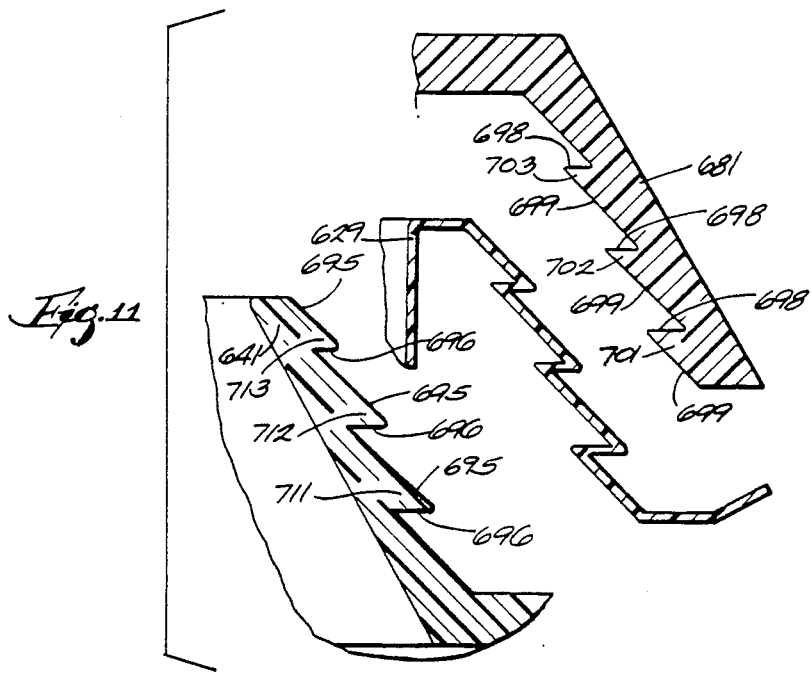
FIG. 11 is an enlarged, exploded, fragmentary sectional view of the apparatus shown in FIG. 10.

An apparatus 600 which overcomes this difficulty is illustrated in FIGS. 10 and 11. The apparatus 600 includes an upper cover member 633 including a vacuum passage 673 and a fluid passage 675. The upper cover member 633 also includes a frustoconical section 681 having thereon a non-threaded serrated formation 693 including a plurality of vertically spaced and horizontally offset projections. In the illustrated construction, the upper cover member 633 includes (see FIG. 11) a lower projection 701, a middle projection 702, and an upper projection 703. The middle projection 702 is offset radially inwardly from the lower projection 701, and the upper projection 703 is offset radially inwardly from the middle projection 702. The projections 701, 702 and 703 extend radially inwardly, and each of the projections includes a generally horizontal upper surface 698 and an upwardly sloped lower surface 699. The lower surfaces 699 preferably slope upwardly at an angle of approximately 45°. The projections 701, 702 and 703 are annular and endless and define grooves there between.

The apparatus 600 also comprises (see FIG. 10) a lower cover member 623 having therein a groove 653 and having thereon a foot 655. The lower cover member 623 includes a frustoconical section 641 which is located inside the section 681 on the upper cover member 633 when the cover members are assembled. The section 641 of the lower cover member 623 has thereon a non-threaded serrated formation 691 including a plurality of vertically spaced and horizontally offset projections. In the illustrated construction, the lower cover member 623 has thereon (see FIG. 11) a lower projection 711, a middle projection 712, and an upper projection 713. The middle projection 712 is offset radially inwardly from the lower projection 711, and the upper projection 713 is offset radially inwardly from the middle projection 712. The projections 711, 712 and 713 extend radially outwardly, are annular and endless, and define grooves there between. Each of the projections 711, 712 and 713 has a downwardly sloped upper surface 695 and a generally horizontal lower surface 696.

When the cover members 623 and 633 are assembled, the bag 629 is clamped between the projections on the upper and lower cover members 623 and 633, and the projections on each of the cover members 623 and 633 are received in the grooves of the other cover member. During assembly of the cover members, each of the projections 711, 712 and 713 on the lower cover member 623 engages, through the bag 629, only the associated projection 701, 702 or 703 on the upper cover member 633. This simplifies assembly of the cover members.

Various of the features of the invention are set forth in the following claims.

We claim:

1. A disposable cover and bag assembly comprising a lower cover member including a top having therein an opening, an upper cover member closing said opening in said top of said lower cover member, and a bag having a mouth gripped between said cover members, one of said cover members being adapted to be connected to the open end of an outer canister, and said cover members including inter-engaging means affording assembly of said cover members and preventing disassembly of said cover members, said inter-engaging means comprising a non-threaded serrated formation on each of said cover members, each of said serrated formations including a plurality of parallel, annular projections defining grooves there between, said projections of each of said formations being received in said grooves of the other of said formations, and said bag being clamped between said formations.

2. A disposable cover and bag assembly comprising an outer cover member adapted to be connected to the open end of an outer canister and having a top including therein an opening, an inner cover member in said opening in said top of said outer cover member, and a bag having a mouth gripped between said inner and outer cover members, said inner and outer cover members including inter-engaging means affording assembly of said inner and outer cover members and preventing disassembly of said inner and outer cover members, said inter-engaging means comprising a non-threaded serrated formation on each of said inner and outer cover members, each of said serrated formations including a plurality of parallel, annular projections defining grooves there between, said projections of each of said formations being received in said grooves of the other of said formations, and said bag being clamped between said formations.

3. A disposable cover and bag assembly in accordance with claim 2 wherein said bag is fabricated of one material and at least one of said cover members is fabricated of a second material different from said one material.

4. A disposable cover and bag assembly in accordance with claim 3 wherein said bag is fabricated of polyvinylchloride.

5. A disposable cover and bag assembly in accordance with claim 3 wherein said at least one of said cover members is fabricated of polyethylene.

6. A disposable cover and bag assembly in accordance with claim 2 wherein said outer cover member includes a cylindrical section including an end surface and an inner surface including, adjacent said end surface, said serrated formation on said outer cover member.

7. A disposable cover and bag assembly in accordance with claim 6 wherein said cylindrical section includes an end opposite said end surface, and an outer surface, and an annular supporting section extending from said outer surface of said cylindrical section in spaced relation from said end and including a cylindrical portion extending in generally parallel relation to said cylindrical section and toward said end and defining there between an annular space for receipt therein of a portion of the canister, said cylindrical portion including an outer end, and said supporting section including an annular foot at said outer end of said cylindrical portion and adapted to rest on a supporting surface.

8. A disposable cover and bag assembly in accordance with claim 6 wherein said inner cover member includes a main body having an outer rim engaging said end surface of said cylindrical section of said outer cover member and a cylindrical section extending from said main body inwardly of said outer rim and having an outer surface with said serrated formation of said inner cover member.

9. An assembly in accordance with claim 2 wherein said inner cover member includes a passage through which a suction can be drawn.

10. A disposable cover and bag assembly in accordance with claim 2 wherein said inner cover member includes a passage through which a fluid can pass through said inner cover member.

11. A collection apparatus with a disposable portion comprising an outer canister having an open end, an outer cover member detachably connected to said open end and having a top including therein an opening, an inner cover member in said opening in said top of said outer cover member, and a bag extending in said outer canister and having a mouth gripped between said inner and outer cover members, said inner and outer cover members including inter-engaging means affording assembly of said inner and outer cover members and preventing disassembly of said inner and outer cover members, said inner-engaging means comprising a non-threaded serrated formation on each of said inner and outer cover members, each of said serrated formations including a plurality of parallel, annular projections defining grooves there between, said projections of each of said formations being received in said grooves of the other of said formations, and said bag being clamped between said formations.

12. A disposable cover and bag assembly comprising an outer cover member adapted to be connected to the open end of an outer canister and having a top including therein an opening, an inner cover member in said opening in said top of said outer cover member, a bag having a mouth gripped between said inner and outer cover members, and means on said inner and outer cover members for clamping said bag there between, said means including on one of said cover members a serrated formation for snap fittingly engaging the other of said cover members and for clamping said bag between said serrated formation and said other of said cover members.

13. A collection apparatus with a disposable portion comprising an outer canister having an open end, an outer cover member detachably connected to said open end and having a top including therein an opening, an inner cover member in said opening in said top of said outer cover member, a bag extending in said outer canister and having a mouth gripped between said inner and outer cover members, and means on said inner and outer cover members for clamping said bag there between, said means including on one of said cover members a serrated formation for snap fittingly engaging the other of said cover members and for clamping said bag between said serrated formation and said other of said cover members.

14. A disposable cover and bag assembly comprising a lower cover member including a top having therein an opening, an upper cover member closing said opening in said top of said lower cover member, and a bag having a mouth gripped between said cover members, one of said cover members being adapted to be connected to the open end of an outer canister, and said cover members including inter-engaging means affording assembly of said cover members and preventing disassembly of said cover members, said inter-engaging means comprising a serrated formation on each of said cover members, said serrated formation on said lower cover member including a plurality of projections having downwardly sloped upper surfaces and generally horizontal lower surfaces, said serrated formation on said upper cover member including a plurality of projections having upwardly sloped lower surfaces and generally horizontal upper surfaces, and said bag being clamped between said formations.

15. A disposable cover and bag assembly in accordance with claim 14 wherein said upper surfaces of said lower cover member engage, through said bag, said lower surfaces of said upper cover member during assembly of said cover members, and wherein said lower surfaces of said lower cover member engage, through said bag, said upper surfaces of said upper cover member so as to prevent disassembly of said cover members.

16. A disposable cover and bag assembly in accordance with claim 14 wherein said projections are parallel, annular and define grooves there between, said projections of each of said formations being received in said grooves of the other of said formations.

17. A disposable cover and bag assembly in accordance with claim 14 wherein said projections on said lower cover member extend radially inwardly, and wherein said projections on said upper cover member extend radially outwardly.

18. A disposable cover and bar assembly in accordance with claim 14 wherein said projections on said lower cover member extend radially outwardly, and wherein said projections on said upper cover member extend radially inwardly.

19. A disposable cover and bag assembly in accordance with claim 14 wherein said projections on each of said cover members are vertically spaced and horizontally offset.

20. A disposable cover and bag assembly in accordance with claim 19 wherein each of said projections on said upper cover member has an associated projection on said lower cover member, and wherein each of said projections on said upper cover member snaps over, through said bar, only said associated projection during assembly of said cover members.

21. A disposable cover and bag assembly in accordance with claim 19 wherein said projections on said lower cover member extend radially outwardly, and wherein said projections on said upper cover member extend radially inwardly.

22. A disposable cover and bag assembly in accordance with claim 21 wherein the projection immediately upwardly adjacent each projection on said lower cover member is offset radially inwardly from said each projection, and wherein the projection immediately upwardly adjacent each projection on said upper cover member is offset radially inwardly from said each projection on said upper cover member.

* * * * *